(12) United States Patent
Agholme

(10) Patent No.: US 8,921,425 B2
(45) Date of Patent: Dec. 30, 2014

(54) TREATMENT OF FUNGAL INFECTIONS

(75) Inventor: Astrid Agholme, Hedemora (SE)

(73) Assignee: Abbell AB, Vikbolandet (SE)

( * ) Notice: Subject to any disclaimer, the term of this patent is extended or adjusted under 35 U.S.C. 154(b) by 0 days.

(21) Appl. No.: 13/822,072

(22) PCT Filed: Sep. 12, 2011

(86) PCT No.: PCT/SE2011/051101
§ 371 (c)(1),
(2), (4) Date: Mar. 11, 2013

(87) PCT Pub. No.: WO2012/036616
PCT Pub. Date: Mar. 22, 2012

(65) Prior Publication Data
US 2013/0165521 A1    Jun. 27, 2013

Related U.S. Application Data

(60) Provisional application No. 61/383,825, filed on Sep. 17, 2010.

(30) Foreign Application Priority Data

Sep. 17, 2010 (EP) .................... 10177275

(51) Int. Cl.
| A61K 31/08 | (2006.01) |
| A61K 9/00 | (2006.01) |
| A61K 8/34 | (2006.01) |
| A61K 8/36 | (2006.01) |
| A61K 8/92 | (2006.01) |
| A61K 9/08 | (2006.01) |
| A61K 31/19 | (2006.01) |
| A61Q 3/00 | (2006.01) |

(52) U.S. Cl.
CPC ............... A61K 9/0014 (2013.01); A61K 8/345 (2013.01); A61K 8/36 (2013.01); A61K 8/922 (2013.01); A61K 9/08 (2013.01); A61K 31/19 (2013.01); A61Q 3/00 (2013.01)
USPC .......................................... 514/578

(58) Field of Classification Search
CPC ......... A61K 8/345; A61K 8/36; A61K 8/922; A61K 9/08; A61K 31/19; A61K 9/0014; A61Q 3/00
USPC ......................................... 514/578
See application file for complete search history.

(56) References Cited

U.S. PATENT DOCUMENTS

| 6,231,840 B1 | 5/2001 | Buck |
| 6,503,946 B1 | 1/2003 | Agholme |
| 6,517,822 B1 | 2/2003 | Buck |
| 6,664,292 B2 | 12/2003 | Bogart |
| 7,267,888 B1 | 9/2007 | Von Krosigk et al. |
| 2002/0183387 A1 | 12/2002 | Bogart |
| 2003/0143173 A1 | 7/2003 | Buck |
| 2003/0148959 A1 * | 8/2003 | Quirk et al. ...................... 514/15 |
| 2003/0235607 A1 | 12/2003 | Buck |
| 2004/0029961 A1 * | 2/2004 | Von Krosigk et al. ......... 514/494 |
| 2004/0137089 A1 * | 7/2004 | Dinan ............................ 424/744 |
| 2004/0180016 A1 | 9/2004 | Buck |
| 2010/0159035 A1 | 6/2010 | Shemer |
| 2010/0292333 A1 | 11/2010 | Mladenovich |
| 2011/0059985 A1 | 3/2011 | Schmidts et al. |

FOREIGN PATENT DOCUMENTS

| CN | 101690721 A | 4/2010 |
| CN | 101716337 A | 6/2010 |
| EP | 1 709 960 A2 | 10/2006 |
| WO | WO 96/11572 A1 | 4/1996 |
| WO | WO 00/45808 A1 | 8/2000 |
| WO | WO 2007/113830 A2 | 10/2007 |
| WO | WO 2009/053741 A2 | 4/2009 |
| WO | WO 2010/130028 A1 | 11/2010 |

OTHER PUBLICATIONS

Lynn Lomasi (2008) http://voices.yahoo.com/10-uses-pure-lemon-essential-oil-1914504.html, accessed Jan. 6, 2014.*
Uses of Glycerin, 1963.*

* cited by examiner

Primary Examiner — Savitha Rao
Assistant Examiner — Angela Brown-Pettigrew
(74) Attorney, Agent, or Firm — Birch, Stewart, Kolasch & Birch, LLP

(57) ABSTRACT

The present disclosure relates to compositions comprising formic acid as an active ingredient and a softening agent or emollient for use in the treatment of fungal infections of the skin and/or nail(s) of mammals, as well as methods for treatment utilizing such compositions.

18 Claims, No Drawings

TREATMENT OF FUNGAL INFECTIONS

CROSS-REFERENCE TO RELATED APPLICATIONS

This application is the National Phase of PCT/SE2011/051101 filed on Sep. 12, 2011, which claims priority under 35 U.S.C. 119(e) to U.S. Provisional Application No. 61/383,825 filed on Sep. 17, 2010 and under 35 U.S.C. 119(a) to Patent Application No. 10177275.4 filed in the European Patent Office on Sep. 17, 2010, all of which are hereby expressly incorporated by reference into the present application.

TECHNICAL FIELD

The present disclosure relates to a composition comprising formic acid as an active ingredient for use in the treatment of fungal infections of the skin and/or the nail(s) of a mammal, especially a human being, such as by topical administration of the composition on the affected area.

BACKGROUND

In temperate climate zones most fungal infections are caused by trichomycetes (dermatophytes), while in tropical climate zones, infections by yeast and molds are more common. Regardless of the cause of infection, the fungus attacks the nail and/or skin and makes it brittle and discolored.

There are four different types of nail infections caused by fungi. The most common infection is frequently caused by Trichophyton rubrum and affects the nail bed and the area beneath the nail. Another type of infection affects only the nail surface and creates white or light colored patches. This second type of fungal infection is unusual and represents only about 10% of the reported cases. A third type of fungal infection affects the nail root and usually afflicts persons with impaired immune defense. A fourth, unusual type is caused by an infection of yeast fungi. Infections by yeast most often only affect nails that already are infected or damaged in some way.

The fungi are invasive to the keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Fungal infections of the skin and/or nail(s) are however not very contagious.

Nail fungal infections are one of the hardest forms of external infection to treat, of which infections of toe nails are the most difficult to treat. While current treatments are somewhat effective, they have adverse side-effects, and are contraindicated for patients taking certain drugs. For example, surgical removal of the nail or drilling holes in the nail to allow penetration of anti-fungal topical treatments results in considerable patient discomfort; systemic administration of anti-fungal drugs suffers from the inherent difficulties involved with parenteral administration and may also result in undesirable side-effects; and anti-fungal lacquers (painted on the nail) lack the necessary penetrating power to directly reach the fungal infection.

In U.S. 2002/0183387, one example of a composition for local administration is disclosed. The composition of U.S. 2002/0183387 has low viscosity and comprises an optionally substituted lower alcohol, such as methanol or ethanol, and an optionally substituted lower carboxylic acid, such as acetic acid or propionic acid, for treatment of bacterial or fungal infections of the nail. The composition, suitable for treatment of conditions such as onychomycosis, typically comprises about 50-90% alcohol by weight and about 10-40% carboxylic acid by weight. The composition penetrates through and underneath the nail plate, thereby attacking the infection.

Another example of a composition for local treatment of nail fungal infections is disclosed in EP 1 709 960. Therein, the composition comprises an alkanoic acid (e.g. methanoic acid) and water for treatment of fungal infections of nails. The preferred concentration ratio is one part acid to 16 parts warm water. The composition is administered by foot baths twice daily for 1-3 months. According to the applicants, the composition softens, dissolves and excoriates the surface and excess nail tissue known as keratin debris.

Other related compositions disclosed elsewhere include WO 2007/113830, U.S. Pat. No. 7,267,888, WO 2010/130028 and WO 00/45808.

Thus, there is still a need in the art for improved, simple and effective treatments of fungal infections of the skin and/or nails.

DESCRIPTION

The above drawbacks and deficiencies of the prior art are overcome or alleviated by, in a first aspect, a composition comprising formic acid as an active ingredient and a softening agent or emollient for use in the treatment of fungal infections of the skin and/or nail(s) of mammals.

The composition according to the first aspect is used as a medicament for the treatment of fungal infections on the skin and/or the nails in such a way that an effect is achieved by the composition on the area of infection, 4-5 days after the first application of the composition. The composition of formic acid and softening agent or emollient is quickly absorbed into the skin and/or nail. The softening agent provides softening of the skin and/or the nail(s) and may facilitate absorption of the composition. Moreover, the softening agent may prevent the skin/nail(s) from becoming dry and brittle. The treatment is continued until the skin and/or nail(s) has/have resumed its/their normal appearance and the fungi have disappeared. The duration of the treatment depends on several factors, such as the extent of the infection, the period the infection has been ongoing, the size of the skin area or the number of nails infected and the general immune defense status of the patient to be treated. As the composition according to the first aspect is absorbed very quickly into the skin/nail, no immobilization nor covering of the affected area, i.e. the infected area of the skin or the infected nail(s), is needed.

In one embodiment of the first aspect, there is provided a composition for use in the treatment of fungal infections of the nail(s); a condition called tinea unguium or onychomycosis.

In another embodiment of the first aspect, there is provided a composition for use in the treatment of fungal infections of the skin, such as Athlete's foot, a condition also known as ringworm of the foot or tinea pedis.

The expression "composition comprising formic acid as an active ingredient" as used herein is intended to comprise, in addition to formic acid, also derivatives of formic acid, for example esters or salts thereof, which in connection with the treatment form the active ingredient.

In another embodiment of the first aspect, the concentration of formic acid is within the range of from 10 to 90% by weight, such as from 15 to 85%, from 20 to 80%, from 25 to 75%, from 30 to 70%, from 35 to 65%, from 40 to 60%, or from 45 to 55% by weight. The concentration of formic acid used in the composition according to the first aspect should thus be chosen in such a way that the concentration is well adapted to the specific area of infection and to the part of the body (skin/nail) where the infection is situated. In one embodiment of the composition according to the first aspect, the concentration of formic acid is 50% by weight.

In another embodiment of the composition according to the first aspect, the concentration of formic acid is from about 6% to about 20% by weight, preferably from about 6% to about 10% by weight, especially when infection is situated on the skin.

According to another embodiment of the first aspect, the softening agent or emollient is selected from, but not limited to, the group consisting of propylene glycol, glycerol, glyceryl triacetate, lactic acid, sorbite, isopropyl myristate, isopropyl palmitate, urea, stearic acid, stearyl alcohol cocoglycerides, octyldodecanol, diisopropyl adipate, cetearyl octanoate, isohexadecanol, diisopropyl adipate, isopropyl stearate, isopropyl laurate and 2-ethylhexyl oxystearate. The skilled person is aware of alternative softening agents or emollients that may be included in the composition according to the first aspect. Further, the softening agent or emollient may represent a pharmaceutically acceptable softening agent or emollient. One specific example of a composition for use in the treatment of fungal infections of the skin and/or nail(s) comprises glycerol as a softening agent or emollient.

In another embodiment of the first aspect, the concentration of softening agent or emollient in the composition is within the range of from 10 to 90% by weight, such as from 15 to 85%, from 20 to 80%, from 25 to 75%, from 30 to 70%, from 35 to 65%, from 40 to 60%, or from 45 to 55% by weight. According to one particular embodiment, the concentration of softening agent or emollient in the composition according to the first aspect is 50% by weight.

In a further embodiment, the composition according to the first aspect consists of formic acid as an active ingredient and a softening agent or emollient. The softening agent or emollient to be used in such a composition may be any of the agents listed above, e.g. glycerol.

In another embodiment, the composition further comprises a lubricant, for example in the form of an oil. Non-limiting examples of oils that may be used in the composition of the first aspect include anise oil, bay oil, bergamot oil, borage oil, canola oil, castor oil, cedar oil, cinnamon oil, lard oil, clove oil, coconut oil, corn oil, macadamia nut oil, linseed oil, olive oil, palm oil, peanut oil, sunflower seed oil, soybean oil, sesam oil, avocado oil, basil oil, almond oil, birch oil, cardamom oil, camomile oil, eucalyptus oil, ginger oil, lemon oil, lavender oil, lime oil, mandarin oil, orange oil, rose oil, rosemary oil and apple oil. Typically, lemon oil or apple oil is used, however, it is to be understood that any oil or other substance providing a lubricating effect may be used in the composition. Further, the lubricant may represent a pharmaceutically acceptable lubricant. The lubricant lubricates the affected area and may, in particular if the affected area is a nail, contribute to strengthening the nail. In addition, the lubricant may provide other features to the composition, such as reducing strong odor caused by the formic acid. Depending on the desired lubricating effect, the concentration of lubricant in the composition may be adjusted. Typically, the composition comprises a small amount of lubricant, such as less than 5% by weight or less than 1% by weight.

The composition may be topically administered onto the affected area, i.e. the specific area of infection on the skin or nail(s). To achieve an effective treatment of the infection, the treatment may be repeated once a week for as long as required, i.e. until no sign of infection can be detected. Typically, the treatment may be repeated for from 10 to 40 weeks. In severe cases, the treatment may be repeated several times a week, but this is generally not needed for achieving a good and effective treatment. If the patient is a human being, he or she can treat him- or herself, which makes the treatment both quick and easy. The patient may apply the composition to the infected area by painting or through the use of a cotton pad stick.

The composition of formic acid and softening agent can be used for treating all kinds of fungal infections of the skin and/or nails, preferably infections on feet and hands. Infections of nails include, but are not limited to, tinea unguium or onychomycosis. Infections of skin include, but are not limited to, Athlete's foot (also known as ringworm of the foot or tinea pedis).

The use of a composition comprising formic acid as an active ingredient and a softening agent or emollient for the treatment of the abovementioned fungal infections will bring about quick symptom alleviation and subsequently good healing. Thus, the composition according to the first aspect is very effective for the treatment of fungal infections. Treatment with the composition is painless and has not shown any side-effects, not even after long term use. Moreover, it is has been identified that the composition according to the first aspect has a strengthening effect on the nails.

The skilled man realizes how the effect of the treatment can be maximized. Thus, the composition according to the first aspect can be comprised in each of the following forms of coating: ointments, lotions, suspensions, gels, sprays or in other topical carriers suitable for the treatment, whereby in this context conventional carriers and optional additives are used.

The composition of formic acid and a softening agent according to the first aspect enables foot specialists and therapists as well as patients to, in an inexpensive and effective manner, treat fungal infections of the skin and/or nail(s), such as tinea unguium or onychomycosis or Athlete's foot, also known as ringworm of the foot or tinea pedis.

There is, in a second aspect of the present disclosure, a method for treatment of fungal infections of the skin and/or nail(s) of a mammal by administration of a composition comprising formic acid as an active ingredient and softening agent or emollient.

Such a method may be used for treatment of fungal infections of the nail(s); hence for the treatment of tinea unguium, also called onychomycosis.

The method may further be used for treatment of fungal infections of the skin, such as Athlete's foot, a condition also known as ringworm of the foot or tinea pedis.

In the second aspect, the optional features of the various components of the composition are as described in connection with the immediately preceding composition aspect.

Thus, in one embodiment, the concentration of formic acid in the composition used in the method according to the second aspect is within a range of from 10 to 90% by weight, such as from 15 to 85%, from 20 to 80%, from 25 to 75%, from 30 to 70%, from 35 to 65%, from 40 to 60%, or from 45 to 55% by weight. According to one specific embodiment, the concentration of formic acid in the composition used in the method is 50% by weight.

In another specific embodiment of the composition according to the second aspect, the concentration of formic acid in the composition used in the method is from about 6% to about 20% by weight, preferably from about 6% to about 10% by weight, especially when infection is situated on the skin.

In another embodiment of the second aspect, the softening agent or emollient is selected from, but not limited to, the group consisting of propylene glycol, glycerol, glyceryl triacetate, lactic acid, sorbite, isopropyl myristate, isopropyl palmitate, urea, stearic acid, stearyl alcohol cocoglycerides, octyldodecanol, diisopropyl adipate, cetearyl octanoate, isohexadecanol, diisopropyl adipate, isopropyl stearate, isopropyl laurate and 2-ethylhexyl oxystearate. Further, said softening agent or emollient may represent a pharmaceutically acceptable softening agent or emollient. In a more specific example, glycerol is used as a softening agent in the method according to the second aspect.

The concentration of softening agent or emollient in the composition for use in the method according to the second aspect may, as described in connection with the first aspect, be comprised within the range of from 10 to 90% by weight, such as from 15 to 85%, from 20 to 80%, from 25 to 75%, from 30 to 70%, from 35 to 65%, from 40 to 60%, or from 45 to 55% by weight. According to one particular embodiment, the concentration of softening agent or emollient in the composition to be used in the second aspect is 50% by weight In a further embodiment of the second aspect, the composition to be used in the method for treatment of fungal infections consists of formic acid as an active ingredient and a softening agent or emollient, for example a softening agent or emollient selected from the group mentioned above.

In addition, the composition to be used in the method may optionally comprise a lubricant, such as an oil, including, but not limited to, anise oil, bay oil, bergamot oil, borage oil, canola oil, castor oil, cedar oil, cinnamon oil, lard oil, clove oil, coconut oil, corn oil, macadamia nut oil, linseed oil, olive oil, palm oil, peanut oil, sunflower seed oil, soybean oil, sesam oil, avocado oil, basil oil, almond oil, birch oil, cardamom oil, camomile oil, eucalyptus oil, ginger oil, lemon oil, lavender oil, lime oil, mandarin oil, orange oil, rose oil, rosemary oil and apple oil. Typically, lemon oil or apple oil is used, however, it is to be understood that any oil or other substance providing a lubricating effect may be used. Further, said lubricant may represent a pharmaceutically acceptable lubricant. Typically, only a small amount of lubricant is comprised in the composition according to this embodiment, such as less than 5% by weight or less than 1% by weight of lubricant.

In another embodiment of the second aspect, the affected area is treated by topical administration of the composition comprising formic acid and softening agent or emollient. Topical administration may for example be achieved by painting or through the use of a cotton pad stick. The composition may for example be administered topically onto the affected area once a week for as long as required, i.e. until no sign of infection can be detected. Typically, the treatment may be repeated for from 10 to 40 weeks. In severe cases, the treatment may be repeated several times a week, but this is generally not needed for achieving a good and effective treatment. If the patient is a human being, he or she can treat him- or herself, which makes the treatment both quick and easy.

In a third aspect of the invention, there is provided a composition comprising formic acid as an active ingredient and a softening agent or emollient for cosmetic treatment of nails of mammals, especially human beings. It has surprisingly been found that when a composition according to the present disclosure is applied to non-infected nails, it improves the appearance of and strengthens the nail. Further, it has surprisingly been identified that when a composition according to the present disclosure is applied to infected nails, it also improves the appearance of and strengthens the nail, when the treatment of the infection is terminated. Such a composition for cosmetic treatment may preferably comprise a lubricant in a small amount, such as an oil. Further optional features of the various components of the composition for cosmetic treatment are as described in connection with the composition according to the first aspect.

In one embodiment of the third aspect, the concentration of formic acid is within the range of from 10 to 90% by weight, such as from 15 to 85%, from 20 to 80%, from 25 to 75%, from 30 to 70%, from 35 to 65%, from 40 to 60%, or from 45 to 55% by weight. According to one particular embodiment, the concentration of formic acid is 50% by weight.

In another embodiment of the third aspect, the concentration of softening agent or emollient in the composition is within the range of from 10 to 90% by weight, such as from 15 to 85%, from 20 to 80%, from 25 to 75%, from 30 to 70%, from 35 to 65%, from 40 to 60%, or from 45 to 55% by weight. According to one particular embodiment, the concentration of softening agent or emollient in the composition according to the third aspect is 50% by weight.

In a further embodiment, the composition according to the third aspect consists of formic acid as an active ingredient and a softening agent or emollient. The softening agent or emollient to be used in such a composition may be any of the agents listed above in connection with the first aspect of the disclosure, e.g. glycerol.

In another embodiment, the composition further comprises a lubricant, for example in the form of an oil, including, but not limited to, anise oil, bay oil, bergamot oil, borage oil, canola oil, castor oil, cedar oil, cinnamon oil, lard oil, clove oil, coconut oil, corn oil, macadamia nut oil, linseed oil, olive oil, palm oil, peanut oil, sunflower seed oil, soybean oil, sesam oil, avocado oil, basil oil, almond oil, birch oil, cardamom oil, camomile oil, eucalyptus oil, ginger oil, lemon oil, lavender oil, lime oil, mandarin oil, orange oil, rose oil, rosemary oil and apple oil. Typically, lemon oil or apple oil is used, however, it is to be understood that any oil or other substance providing a lubricating effect may be used. Further, said lubricant may represent a pharmaceutically acceptable lubricant. The lubricant lubricates, strengthens and improves the appearance of the nail. In addition, the lubricant may provide other features to the composition, such as reducing strong odor caused by the formic acid. Typically, the composition comprises a small amount of lubricant, such as less than 5% by weight or less than 1% by weight.

The composition may be topically administered onto the nails. The treatment may be repeated once a week for as long as required. The treatment may be repeated several times a week, but this is generally not needed for achieving a good and effective cosmetic treatment. If the patient is a human being, he or she can easily. The patient may apply the composition to the nails by painting or through the use of a cotton pad stick.

The use of a composition comprising formic acid as an active ingredient and a softening agent or emollient for the cosmetic treatment of the nails will bring about quick improvement of nail quality. Thus, the composition according to the third aspect is very effective for the cosmetic treatment of the nails. Treatment with the composition is painless and has not shown any side-effects, not even after long term use.

The skilled man realizes how the effect of the cosmetic treatment can be maximized. Thus, the composition according to the first aspect can be comprised in each of the following forms of coating: ointments, lotions, suspensions, gels, sprays or in other topical carriers suitable for the treatment, whereby in this context conventional carriers and optional additives are used.

The composition of formic acid and a softening agent according to the third aspect enables foot and hand specialists and therapists as well as patients to, in a cheap and effective manner, cosmetically treat nails.

In addition, there is provided, in a fourth aspect, a method for cosmetic treatment of nails of mammals, such as human beings, by topical administration of a composition comprising formic acid as an active ingredient and a softening agent or emollient. Optional features and embodiments of this fourth aspect are as described above in connection to the second (method) aspect.

In one embodiment, the concentration of formic acid in the composition used in the method according to the fourth aspect is within the range of from 10 to 90% by weight, such as from 15 to 85%, from 20 to 80%, from 25 to 75%, from 30 to 70%, from 35 to 65%, from 40 to 60%, or from 45 to 55% by weight. According to one specific embodiment, the concentration of formic acid in the composition used in the method is 50% by weight.

In another embodiment of the fourth aspect, softening agent or emollient is selected from, but not limited to, the group consisting of propylene glycol, glycerol, glyceryl triacetate, lactic acid, sorbite, isopropyl myristate, isopropyl palmitate, urea, stearic acid, stearyl alcohol cocoglycerides, octyldodecanol, diisopropyl adipate, cetearyl octanoate, isohexadecanol, diisopropyl adipate, isopropyl stearate, isopropyl laurate and 2-ethylhexyl oxystearate. Further, said softening agent or emollient may represent a pharmaceutically acceptable softening agent or emollient. In a more specific example, glycerol is used as a softening agent in the method according to the fourth aspect. The concentration of softening agent or emollient in the composition for use in a method according to the fourth aspect may, as described in connection with the first aspect, be comprised within the range of from 10 to 90% by weight, such as from 15 to 85%, from 20 to 80%, from 25 to 75%, from 30 to 70%, from 35 to 65%, from 40 to 60%, or from 45 to 55% by weight. According to one particular embodiment, the concentration of softening agent or emollient in the composition to be used in the fourth aspect is 50% by weight In a further embodiment of the fourth aspect, the composition to be used in the method for cosmetic treatment consists of formic acid as an active ingredient and a softening agent or emollient, for example a softening agent or emollient selected from the group mentioned above.

In addition, the composition to be used in the method may optionally comprise a lubricant, such as an oil, including, but not limited to, anise oil, bay oil, bergamot oil, borage oil, canola oil, castor oil, cedar oil, cinnamon oil, lard oil, clove oil, coconut oil, corn oil, macadamia nut oil, linseed oil, olive oil, palm oil, peanut oil, sunflower seed oil, soybean oil, sesam oil, avocado oil, basil oil, almond oil, birch oil, cardamom oil, camomile oil, eucalyptus oil, ginger oil, lemon oil, lavender oil, lime oil, mandarin oil, orange oil, rose oil, rosemary oil and apple oil. Typically, lemon oil or apple oil is used, however, it is to be understood that any oil or other substance providing a lubricating effect may be used. Further, said lubricant may represent a pharmaceutically acceptable lubricant. The lubricant lubricates the nail and may further strengthen and improve the appearance of the nail. In addition, the lubricant may provide other features to the composition, such as reducing strong odor caused by the formic acid. Depending on the desired lubricating effect, the concentration of lubricant in the composition may be adjusted. Typically, the composition comprises a small amount of lubricant, such as less than 5% by weight or less than 1% by weight.

In another embodiment of the fourth aspect, the nails are treated by topical administration of the composition comprising formic acid and softening agent or emollient. Topical administration may for example be achieved by painting or through the use of a cotton pad stick. The composition may for example be administered topically onto the nails once a week for as long as required. Thus, in further embodiments, the composition is topically administered on the nails, such as once a week. If the patient is a human being, he or she can easily treat him- or herself.

In addition to the above described aspects, there is provided a composition according to the invention, comprising formic acid as an active ingredient at a concentration of about 50% by weight and glycerol as softening agent or emollient at a concentration of about 50% by weight, and optionally further comprising a lubricant, such as an oil.

The invention will be further illustrated below by specific examples, which are not in any way intended to limit the scope of protection of the invention.

EXAMPLES

Method of Administration onto Nails

In the following, a standard procedure for administering the composition of the present disclosure to the nail of a human being is accounted for.

The infected nail was firstly softened with hot water for approximately 10-15 minutes. The composition was evenly administered to the surface of the infected nail by painting with a cotton pad stick. Alternatively, the composition may be applied by painting with a brush. The composition should be applied onto the nail and nail cuticle (eponychium) only, and thereby not potentially irritate the area outside the nail. In addition, a small amount of composition was applied under the nail by using a cotton pad stick.

The composition was applied onto the nails with a week's interval. When the treatment was repeated, the nail cuticle (eponychium) was also carefully painted with the composition. This prevented the infection from spreading to the growing part of the nail.

In cases of severe infection, the nail was pre-treated by slight smoothing or rubbing with a nail file. This nail surface treatment may influence the absorption of the composition and this may be useful when the infected nail is thick and/or cracked.

The composition amount applied to the nail was, from patient to patient, adjusted to the size of the nail and the severity of the infection.

Treatment of Patients Suffering from Fungal Infections on the Nails:

To illustrate the efficiency of the composition comprising formic acid as an active ingredient and softening agent or emollient according to aspects as described herein, the composition has been tested on persons suffering from fungal infections. Below, treatment of 15 patients is described and the result of the treatment presented (Table 1).

The patients were treated either by themselves (at home) or under surveillance (at clinic). The method of administration as described above was used/recommended to the patients. All patients had confirmed fungal infections (by test at clinic/hospital) for at least one year prior the start of the treatment.

A composition for treating the fungal infections was prepared by mixing approximately 50% formic acid with approximately 50% glycerol. A few drops of apple oil were added to the mixture.

TABLE 1

| Patient | Sex (F/M) | Affected area | Origin/duration of infection | Number of treatments | Treated at clinic/at home | Result |
|---|---|---|---|---|---|---|
| 1 | F | Foot, 3 toes | ca 1 year | 25 | C | Eliminated |
| 2 | F | Foot, big toe | ca 1.5 years | 20 | C + H | Eliminated |
| 3 | M | Foot, 2 toes | ca 3 years | 18 | C + H | Eliminated |
| 4 | M | Feet, 2 toes/foot | ca 2 years | 30 | H | Eliminated |
| 5 | M | Hand, 1 nail | ca 2 years | 35 | H | Eliminated |
| 6 | M | Hands, 2 thumbs | ca 2-3 years | 20 | H | Eliminated |
| 7 | F | Foot, 2 toes | ca 2 years | 40 | C + H | Eliminated |
| 8 | M | Foot, 4 toes | ca 1 year | 30 | H | Eliminated |
| 9 | M | Foot, 1 toe | ca 1 year | 35 | H | Eliminated |
| 10 | F | Hand, little finger | ca 1 year | 10 | H + C | Eliminated |
| 11 | M | Foot, 4 toes | ca 2 years | 25 | H + C | Eliminated |
| 12 | F | Foot, 2 toes | ca 1 year | 28 | H | Eliminated |
| 13 | F | Foot, 2 toes | ca 1.5 years | 15 | C | Eliminated |
| 14 | F | Foot, 3 toes | ca 3 years | 17 | C | Eliminated |
| 15 | M | Foot, 1 big toe | 1 year | 15 | C | Eliminated |

The treatment was repeated until the infection was eliminated, typically after 15-30 rounds of treatment. The number of treatments required depended on the number of nails infected, the nature of the infection and how long the patient had suffered from the infection. After completed treatment, patients reported that their nails were shiny, healthy and strengthened. No allergies or side effects were observed. For all patients above, in addition to elimination of the infection, the general quality of the nails was significantly increased.

The conclusion that can be drawn from the results given above is that the nail fungi were eliminated after treatment according to the method and with the composition as disclosed herein. Further it is concluded that treatment according to the methods disclosed and compositions disclosed herein is useful in cosmetic treatment of nails, also for non-infected nails.

The invention claimed is:

1. A method for treatment of at least one fungal infection of the skin and/or nail(s) of a mammal, comprising:
    administering a composition consisting of formic acid, glycerol and optionally a lubricant,
    wherein a concentration of formic acid is within the range of from 50 to 70% by weight, and
    wherein a concentration of glycerol is within the range of from 30 to 50% by weight.

2. The method according to claim 1, wherein said method is for treatment of at least one fungal infection of the nail(s).

3. The method according to claim 1, wherein said method is for treatment of at least one fungal infection of the skin.

4. The method according to claim 3, wherein the at least one fungal infection of the skin represent Athlete's foot.

5. The method according to claim 1, wherein the concentration of formic acid is within the range of from 50 to 60% by weight.

6. The method according to claim 5, wherein the concentration of formic acid is 50% by weight.

7. The method according to claim 1, wherein the composition contains the lubricant.

8. The method according to claim 7, wherein the lubricant is present in an amount of less than 5% by weight.

9. The method according to claim 8, wherein the lubricant is an oil.

10. The method according to claim 9, wherein the oil is selected from the group consisting of apple oil and lemon oil.

11. The method according to claim 1, wherein the composition is topically administered onto an affected area.

12. The method according to claim 11, wherein the composition is topically administered onto the affected area once a week.

13. The method according to claim 1, wherein the composition is administered to the skin and/or nail(s) by painting.

14. The method according to claim 1, wherein the mammal is a human.

15. The method according to claim 1, wherein glycerol is present in the composition in an amount within the range of from 40 to 50% by weight.

16. The method according to claim 15, wherein glycerol is present in the composition in an amount of 50% by weight.

17. The method according to claim 1, wherein the concentration of formic acid is 70% by weight.

18. The method according to claim 1, wherein the composition is topically administered for 10 to 40 weeks.

* * * * *